United States Patent [19]
Gazzi et al.

[11] Patent Number: 4,514,203
[45] Date of Patent: Apr. 30, 1985

[54] CRYOGENIC PROCESS FOR REMOVING ACIDIC GASES FROM GAS MIXTURES

[75] Inventors: Luigi Gazzi, Milan; Giancarlo Cotone, S. Donato Milanese; Gianfraco Soldati, S. Donato Milanese; Alessandro Ginnasi, S. Donato Milanese; Alessandro Vetere, Milan; Carlo Rescalli, S. Donato Milanese, all of Italy

[73] Assignee: Snamprogetti, S.p.A., Milan, Italy

[21] Appl. No.: 391,282

[22] Filed: Jun. 23, 1982

[30] Foreign Application Priority Data
Jul. 23, 1981 [IT] Italy .................. 23081 A/81

[51] Int. Cl.$^3$ .......................... F25J 3/00; F25J 3/02
[52] U.S. Cl. .............................. 62/17; 55/68; 55/73
[58] Field of Search ............... 62/17, 20; 203/42; 55/68, 73; 208/332–334, 329

[56] References Cited
U.S. PATENT DOCUMENTS

| | | | |
|---|---|---|---|
| 1,732,371 | 10/1929 | Luther et al. | 208/329 |
| 2,045,321 | 6/1936 | Clarke | 208/329 |
| 4,302,220 | 11/1981 | Volkamer et al. | 55/73 |

*Primary Examiner*—Frank Sever
*Attorney, Agent, or Firm*—Morgan, Finnegan, Pine, Foley & Lee

[57] ABSTRACT

Low temperature treatments are combined with solvent treatments using particularly selective solvents for stripping acidic gases such as carbon dioxide and hydrogen sulphide from natural gas or from synthetic gases.

The preferred solvents are a wide range of compounds having an esteric or an etheric function in their molecule, but there are also examples of compounds which have the two functions simultaneously.

The stripping process is comparatively simple, is efficient, especially for high contents of acidic gases in the raw gas streams, and is economically acceptable.

20 Claims, 1 Drawing Figure

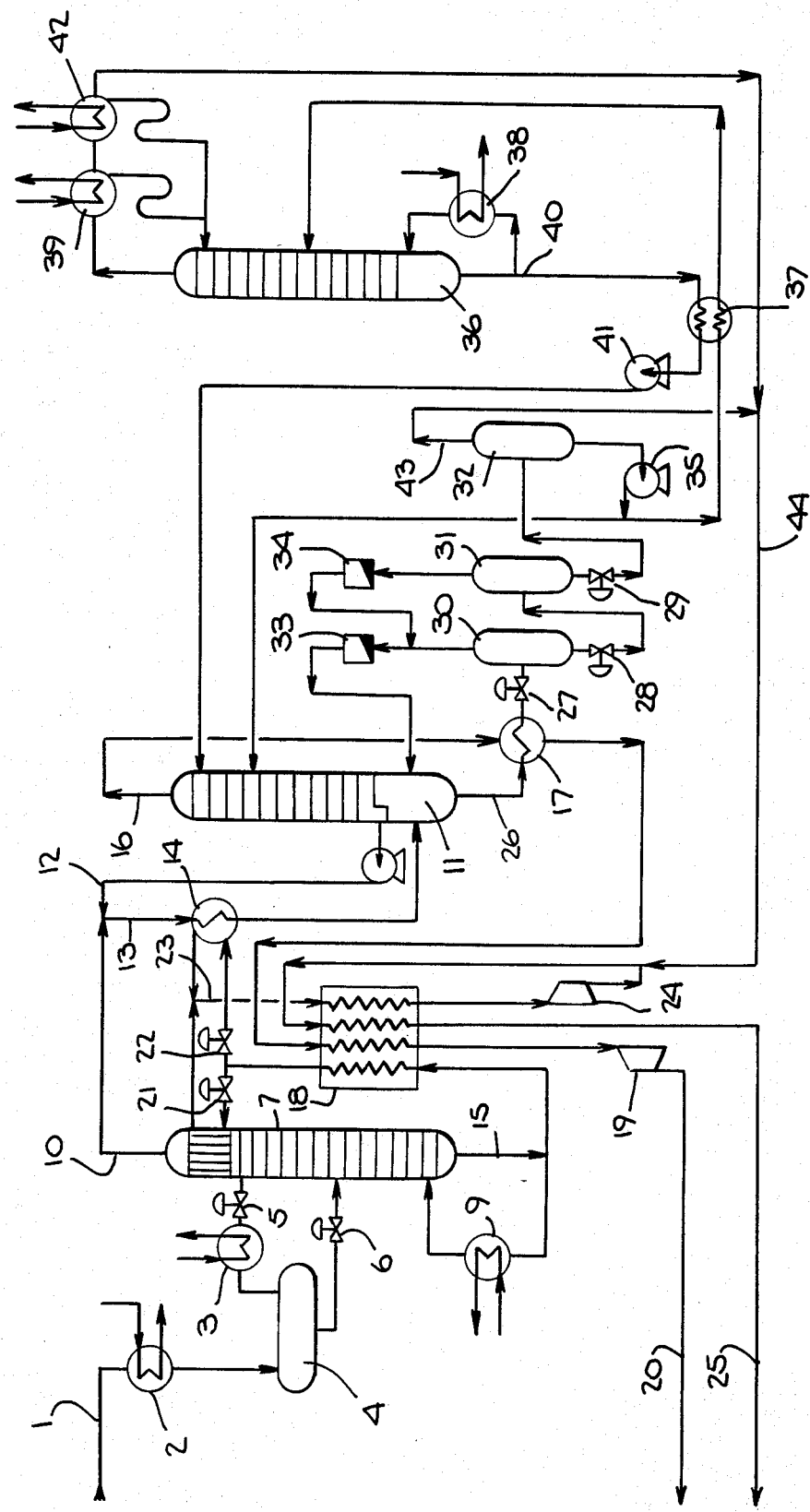

CRYOGENIC PROCESS FOR REMOVING ACIDIC GASES FROM GAS MIXTURES

This invention relates to a process for the removal of acidic gases such as hydrogen sulphide and carbon dioxide from gas mixtures containing them, said process being particularly suitable for treating gaseous mixtures which have acidic gas contents of an even very high magnitude.

The processes of the conventional art for solving such a problem are technologically indicated to treat gases which, in their raw condition, contain comparatively slight percentages of acidic gases.

These conventional processes, in fact, have been influenced by the circumstance that they had been devised in times when the cost of power was relatively low so that only natural gases having low percentages of the acidic components aforesaid were exploited.

Such processes of the conventional technology can of course, be exploited also for treating gases having a high content of acidic components, but the results, both from the economical and the technical viewpoint, can become unacceptable under stringent conditions.

As a matter of fact, these processes are essentially based on the absorption with selective solvents which retain the acidic components and leave the purified gas free.

The cost of the treatment, thus, is, with a fair approximation, proportional to the quantity of solvent which is employed with respect to the volume of gas to be handled. Such quantity of solvent is a growing function of the contents of acidic components. The cost of the treatment must thus be attributed to the purified gas.

It becomes thus apparent that the treatments according to the conventional technology have costs which grow unacceptable as the contents of the acidic gases grows.

Under the present conditions of power shortage, the best course is to exploit the available resources to their best.

To start production in gas fields in which gases with a high contents of acidic components are found, or to purify synthesis gases produced from fuel oil or coal, the necessity is strongly felt for handling processes which are suitable for gases having high and very high contents of acidic components and which can fulfil even very rigorous specifications.

The treatment of gases of the kind referred to above requires the adoption of mixed technologies, that is with cryogenic means and with a solvent so as to combine the advantages of the two routes and to obtain thereby a satisfactory purification of the gases concerned at acceptable costs.

The present Applicants have already claimed a process of the kind referred to above by the British Pat. No. 1,555,068 filed Mar. 3, 1977. The patent in question discloses the purification of a raw gas which contained more than 70% of acidic gases by the combined use of a low-temperature distillation step and an absorption step using a solvent. The solvents described in the patent are dimethyletherpolyglycol and propylene carbonate.

A novel purification process has now been found, which is particularly adapted to treat gases having a high percentage of acidic gases and which exploits a class of selective solvents which are particularly suitable for the purification by a cryogenic cycle.

An object of the present invention is to employ such solvents in the treatment cycle to be described hereinafter.

The solvents to be used in the process according to this invention are, above all, esters and ethers having a low molecular weight and belonging to the following classes:

esters of alcohols of the general formula $R_1COOR_2$ wherein $R_1$ and $R_2$ are alkyls having from 1 to 4 carbon atoms, equal to or different from one another, such as methyl formate, methyl acetate and ethyl acetate;

esters of glycols of the general formula:

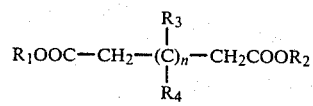

wherein $R_1$ and $R_2$ are alkyls having from 1 to 3 carbon atoms, equal to or different from one another, $R_3$ and $R_4$, equal to or different from one another, are either alkyls having from 1 to 3 carbon atoms, or hydrogen atoms, n is an integer which can be either 0 or 1, such as 1,3-propanediol acetate, and 2,2-dimethylpropanediol diacetate.

cyclic esters (lactones) of the formula:

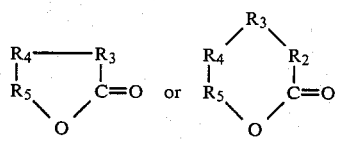

wherein $R_2$, $R_3$, $R_4$, $R_5$, equal to or different from each other, are alkylenes of which the hydrogen can optionally be substituted by alkyls or methoxy groups;

open-chain or cyclic ethers such as:

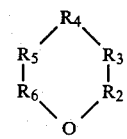

wherein $R_2$, $R_5$, $R_6$, equal to or different from each other, are alkylenes in which the hydrogen can optionally be substituted by alkylene or methoxy groups, $R_3$ can be an oxygen atom or an alkylene group in which the hydrogen can optionally be substituted by alkyl or methoxy groups, $R_4$ can be the same as $R_5$ or be absent in the case of a 5-membered ring, such as tetrahydrofuran, methyltetrahydrofuran, tetrahydropyran, 1,3-dioxolan;

diethers having the general formula:

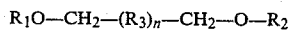

$$R_1O-CH_2-(R_3)_n-CH_2-O-R_2$$

wherein $R_1$ is an alkyl having from 1 to 4 carbon atoms, $R_2$ is hydrogen or an alkyl of from 1 to 4 carbon atoms, or a hydrogen atom, $R_3$ is either an alkylene or a ($CH_2-O-CH_2$) group, n being an integer which can be etiher 0 or 1, such as 1,2-dimethoxyethane, 1,2-methoxyethoxyethane, dimethoxydiethyleneglycol, 1-methoxyethanol;

monoethers having the general formula $R_1-O-R_2$, wherein $R_1$ and $R_2$, equal to or different from one another, are alkyls having from 1 to 4 carbon atoms;

esters-ethers, that are compounds containing both the esteric and the etheric functions, having the general formula:

$$(R_4-O-)_n-R_1-COOR_2-OR_3$$

wherein $R_3$ and $R_4$, equal or different from one another, are alkyls having from 1 to 4 carbon atoms, $R_2$ is an alkylene group having from 1 to 4 carbon atoms, $R_1$ is the same as $R_2$ or the same as $R_3$, n is an integer which can be either 0 or 1, such as 2-methoxyethyl acetate.

The solvents referred to above combine a number of properties which are quite favourable to their use as selective solvents.

As a matter of fact, they have a high stability under the conditions of use, they have a high solvent power relative to the acidic gases, they possess a high selectivity towards $H_2S$ relative to $CO_2$ and the hydrocarbons in general, a high selectivity for $CO_2$ with respect to the hydrocarbons, and, in addition, they have a low molecular weight and a low melting point. The latter characteristic is vital for their use in a cryogenic process.

In the case when a natural gas is being treated, after the low-temperature distillation and prior to the final purification with a solvent, the gas is available at very low temperatures, considerably lower than zero centigrade.

During progress of the final purification, it is an advantage to be able to attain temperatures which are considerably lower than the temperature of the gas, that which is an asset because the absorbing power of the solvent is thereby increased and its selectivity as well. The solvents for the process according to this invention have a low melting point and are thus quite particularly suitable for being used in a cryogenic process.

The solvents referred to above, in addition, have the property of being markedly selective towards hydrogen sulphide as compared with carbon dioxide so that they provide a good measure of safety relatively to the most hazardous component.

The solvents according to the invention can be used alone, or in admixture with each other, or they can be admixed with water and/or with an organic compound having a low melting point, such as dimethyl ether, methanol, acetone with a view to adjust the solvent power as a function of the gases to be treated and the conditions of the gas and of temperature and pressure.

The process according to the invention thus comprises the following steps:

(a) Feeding the natural (or the synthesized) gas to a low-temperature distillation column having the task of reducing the acidic gas contents;

(b) Feeding the partially purified gas exiting the distillation column in (a) to an absorption column so as to further reduce the acidic acid contents down to the desired value;

(c) Regenerating the exhausted solvent(s) exiting the bottom of the absorption column, initially by one or more expansion stages wherefrom the useful components absorbed together in stage (b) are recovered, to be recycled to said absorption column, then by another or several additional expansion stages wherefrom the acidic gases are evolved;

(d) Recycling the regenerated solvent(s) of (c) to the absorption column of stage (b).

The regeneration of the solvent, stage (c), after the expansion stages, must be completed by a distillation column if the acidic gases contain also hydrogen sulphide, inasmuch as the specifications for the residual $H_2S$ in the treated gas are much more drastic than those for $CO_2$ alone; conversely, if only $CO_2$ is contained in the acidic gases, the use, or nonuse, of a distillation regenerative column just depends on the maximum permissible contents of carbon dioxide in the purified gas.

The distillation column in (a) works under a pressure ranging from 30 and 75 abs.atm. preferably between 35 and 55 abs.atm., whereas the temperature of the column head must be selected between $-80°$ C. and $-30°$ C. and the temperature of the column bottom must be between $-7°$ C. and $+50°$ C.

The absorption column of (b) works under the same pressure (pressure drops not included) as the previous distillation column, that is, between 30 and 75 abs.atm. whereas the temperature must be selected between $-100°$ C. and $-10°$ C.

The expansion stages of (c) can be, in total, from 2 to 6, the last stage working under a pressure comprised between 0.2 and 2 abs.atm.

If also a distillation column is provided for the regeneration stage, said column will work under a pressure comprised between 1.1 and 3 abs.atm. at a head temperature of from 30° C. and 50° C., the bottom temperature being between 55° C. and 100° C.

If only $CO_2$ is present, the temperature ranges for the operation of the low-temperature distillation column must be narrower than aforesaid.

As a matter of fact, under these conditions, the head temperature of the low-temperature distillation column is comprised between $-57°$ C. and $-30°$ C., and the column bottom temperature is from $-7°$ C. and $+31°$ C.

Furthermore, still in the case in which only $CO_2$ is present, if the specifications as to the contents of $CO_2$ in the purified gas are not too stringent, so that non end distillation column is necessary, the last expansion stage works under a pressure which is comprised between 0.2 and 0.9 abs. atmospheres.

The invention will now be explained with the aid of the accompanying drawing the single FIGURE of which shows an embodiment which should not be regarded as a limitation of the invention.

The drawing is illustrative of a process whereby natural gas is stripped of both $CO_2$ and $H_2S$.

The natural gas fed through the pipeline 1, is cooled and optionally split into two (or more) fractions by fractional condensation, using heat exchangers 2 and 3 and a separator 4. The two fractions are fed by the valves 5 and 6 to the low-temperature distillation column 7, which is equipped with a dephlegmator 8 and a reboiler 9 which is heated by condensing a portion of a refrigerating fluid. The column 7 has the task of reducing the contents of acidic gases to 5%–30% molar.

If a pressure differential of at least 3 atm exists between the pressure of the raw gas and the working pressure of the column 7, the gas, or the fraction of it which is left in the vapour state after pre-cooling or fractional condensation can be caused to expand within a turbine so as to produce both negative calories and power.

The gas 10 exiting the top of the distillation column is combined, prior to being fed to the absorption column 11, with a portion of the exhausted solvent 12, drawn from the last plate of said absorption column.

The thus formed mixture 13, is cooled in the heat exchanger 14 by a portion of the liquid stream 15 of acidic gases as produced by the low-temperature distillation column and is sent to a separator, which is placed, in the diagram of this example, at the bottom of the absorption column, and the separator furnishes the solvent to be regenerated as well as the partially purified gas to be fed under the last plate of the absorption column.

The purified gas 16, which now contains not more than a few tens of parts per million (ppm) of $CO_2$ and a few fractions of ppm of $H_2S$, exits the column 11 and is heated in the exchangers 17 and 18 so as to recover negative calories and is compressed to the pressure of use in the compressor 19 prior to leaving the installation via the pipeline 20. From the bottom of the low-temperature distillation column 7, a liquid stream 15 is drawn, which essentially contains $CO_2$ and $H_2S$, which is undercooled in the exchanger 18 and optionally split into two streams: either stream is expanded by the valve 21 and vaporized in the dephlegmator 8, the other stream being expanded through the valve 22 and vaporized in the exchanger 14 so as to cool the mixture 13.

If the stream which contains $CO_2$ and $H_2S$ is not split, the whole stream is expanded through the valve 21 and vaporized in the dephlegmator 8. The expansion through the two valves takes place under a pressure of from 1 abs.atm. to 8 abs.atm.

The two vaporized streams are combined to make up a single stream 23, which is heated at 18, expanded through the turbine 24, heated at 18 again and lastly sent out of the installation via a pipeline 25.

From the bottom of the absorption column 11 a stream 26 is drawn, which contains the solvent, the carbon dioxide, the $H_2S$ and useful components, such as methane.

To regenerate the solvent contained therein, the stream in question, after having been cooled at 17, is expanded through a number of expansion stages (three in the case in point) through the valves 27, 28 and 29 and the separators 30, 31 and 32. From the first two separators, 30 and 31, a gas is evolved which is still rich with methane and which is recycled by the compressors 33 and 34 to the absorption column 11. From the bottom of the third separator 32, a stream is drawn, which is sent by the pump 35 partly to the absorption column and particularly to the distillation column 36, after having been heated in an exchanger 37, whereby the solvent regeneration is completed. The distillation column 36 is equipped with a reboiler 38 and a condenser 39. From the bottom of the distillation column 36, a stream 40 is drawn which essentially consists of the regenerated solvent and, which, after having been cooled at 37, is fed by a pump 41 to the absorption column 11.

Through the head of the distillation column 36 a gaseous stream emerges, which essentially contains $CO_2$ and $H_2S$, and which, after having been cooled in the exchanger 42 is admixed with the gaseous stream 43 exiting the head of the last separator: the stream which is formed in this way, 44, is admixed, in its turn, with the stream coming from the turbine 24 and leaves the installation through the pipeline 25 after having been heated at 18. Optionally, the turbine 24 can be replaced by a valve.

We claim:

1. A cryogenic process for removing acidic gases, such as $H_2S$ and $CO_2$, from natural gas or syngas consisting the steps of:
   (a) feeding the natural gas or syngas to a distillation column under a pressure of from 30 to 75 absolute atmospheres at a head temperature between $-80°$ C. and $-30°$ C. and a bottom temperature between $-7°$ C. and $+50°$ C.;
   (b) feeding the partially purified gas exiting from the distillation column with a solvent for selective absorption of acidic gases, the solvent being selected from the group consisting of methyl formate, methyl acetate, ethyl acetate, tetrahydropyran, 1,3-dioxolane, tetrahydrofuran, methyltetrahydrofuran, 1,2-dimethoxyethane, 1-methoxyethanol, 2-methoxyethylacetate and dimethoxydiethyleneglycol and mixtures thereof; to an absorption column under the same pressure as the distillation column and at a temperature between $-100°$ C. and $-10°$ C. to further reduce the acidic gas content to a desired level;
   (c) regenerating the spent solvents from said absorption column by one or more expansion stages to recover the solvents;
   (d) removing the acidic gases by one or more additional expansion stage; and
   (e) recycling the recovered solvents to said absorption column.

2. A process according to claim 1, wherein the pressure is comprised between 35 and 55 abs.atm.

3. A process according to claim 1, wherein the expansion stages of (c) can be in total from 2 to 6.

4. A process according to claims 1 or 3, wherein the last separator of (c) works under a pressure comprised between 0.2 and 2 abs. atmospheres.

5. A process according to claim 1, characterized in that in addition to the expansion stages of (c) the regeneration of the solvent is completed by a regenerative distillation column from the head of which the acidic gases emerge.

6. A process according to claims 1 or 5, wherein the regenerative distillation column works under a pressure comprised between 1.1 and 3 abs. atmospheres at a head temperature between 30° C. and 50° C. and a bottom temperature between 55° C. and 100° C.

7. A process according to claim 1, characterized in that the liquefied acidic gas stream drawn from the bottom of the low-temperature distillation column of (a) is undercooled in an exchanger, expanded and vaporized, totally or partially, in the condenser of the distillation column and, for the possible partial portion in an exchanger, the acidic gas stream(s) thus obtained being heated in the same exchanger as for the liquid stream, further expanded in a valve or a turbine and finally heated again in the same exchanger of the liquified acidic gas stream.

8. A process according to claims 1 or 7, characterized in that the pressures at which the acidic gases are expanded after having been undercooled is comprised between 1 and 8 abs.atm. and that the pressure at which the acidic gases are expanded after having been vaporized and heated is about the atmospheric pressure.

9. A process according to claim 1, characterized in that the natural or the synthesis gas prior to being sent to the low-temperature distillation column of (a) is split into two or more fractions by fractional condensation.

10. A process according to claim 1, characterized in that the natural or the synthesis gas or the portion thereof which is left in the vapour state after precooling or fractional condensation, prior to being sent to the low-temperature distillation column can be expanded in a turbine.

11. A process according to claim 1, wherein the low-temperature distillation column, in the case in which only $CO_2$ is present, works at a head temperature comprised between $-57°$ C. and $-30°$ C. and at a bottom temperature comprised between $-7°$ C. and $+31°$ C.

12. A process according to claim 1, characterized in that a part of the exhausted solvent drawn from the last plate of the absorption column of (b) is combined with the gas coming from the low-temperature distillation column of (a) and that the so-formed mixture is cooled in an exchanger by a portion of the liquid stream of acidic gases produced by the low-temperature distillation column and sent to a separator wherefrom there are obtained the solvent to be regenerated and the partially purified gas which is fed to the same absorption column.

13. A process according to claim 1, wherein water and/or an organic compound having a low melting point is added to the selective solvent.

14. A process according to claim 1 or 13 wherein the organic compound having a low melting point is added in a proportion comprised between 0.3% and 40% of the resultant mixture.

15. A process according to claim 13 wherein the organic compound is selected from the group comprising methanal, dimethylether and acetone.

16. A process according to claim 1 wherein the solvent for selective absorption is selected from the group consisting of methyl formate, methyl acetate and ethyl acetate.

17. A process according to claim 1 wherein the solvent for selective absorption is selected from the group consisting of tetrahydropyran, 1,3-dioxolane, tetrahydrofuran, and methyltetrahydrofuran.

18. A process according to claim 1 wherein the solvent for selective absorption is selected from the group consisting of the diacetate of 1,3-propanediol and the diacetate of 2,2-dimethyl-1,3-propanediol.

19. A process according to claim 1 wherein the solvent for selective absorption is selected from the group consisting of dimethoxydiethyleneglycol and 1-methoxyethanol.

20. A process according to claim 1 wherein the solvent for selective absorption is 2-methoxyethylacetate.

* * * * *